United States Patent
Zhen

(10) Patent No.: US 10,449,141 B2
(45) Date of Patent: Oct. 22, 2019

(54) GEL NAIL POLISH AND ITS MANUFACTURING AND USING METHOD

(71) Applicant: Lijuan Zhen, City of Industry, CA (US)

(72) Inventor: Lijuan Zhen, City of Industry, CA (US)

(*) Notice: Subject to any disclaimer, the term of this patent is extended or adjusted under 35 U.S.C. 154(b) by 158 days.

(21) Appl. No.: 14/839,926

(22) Filed: Aug. 29, 2015

(65) Prior Publication Data

US 2017/0056306 A1    Mar. 2, 2017

(51) Int. Cl.
| | |
|---|---|
| *A61K 8/40* | (2006.01) |
| *A61Q 3/02* | (2006.01) |
| *A61K 8/34* | (2006.01) |
| *A61K 8/55* | (2006.01) |
| *A61K 8/36* | (2006.01) |
| *A61K 8/81* | (2006.01) |
| *A61K 8/04* | (2006.01) |
| *A61K 8/37* | (2006.01) |
| *A61K 8/87* | (2006.01) |

(52) U.S. Cl.
CPC ............ *A61K 8/8147* (2013.01); *A61K 8/042* (2013.01); *A61K 8/345* (2013.01); *A61K 8/36* (2013.01); *A61K 8/375* (2013.01); *A61K 8/40* (2013.01); *A61K 8/87* (2013.01); *A61Q 3/02* (2013.01); *A61K 2800/596* (2013.01); *A61K 2800/805* (2013.01); *A61K 2800/81* (2013.01); *A61K 2800/882* (2013.01); *A61K 2800/884* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 2011/0060065 A1* | 3/2011 | Vu ..................... | A61K 8/8152 521/149 |
| 2013/0146077 A1* | 6/2013 | Cooke .................. | A61K 8/37 132/200 |
| 2015/0190331 A1* | 7/2015 | Chang ................. | A61K 8/8152 424/61 |

* cited by examiner

*Primary Examiner* — Nicole P Babson
(74) *Attorney, Agent, or Firm* — Changi Wu; Changi Wu Law Office

(57) ABSTRACT

A gel nail polish composition includes a gel nail polish mixture and a color agent mixing therewith for forming a gel nail polish layer on a nail of a user. The gel nail polish mixture includes first through fourth chemical elements, wherein the first through fourth chemical elements are aliphatic urethane acrylate, polymer acrylate oligomer, propoxylated neopentyl glycol diacrylate, and trimethylbenzoyl diphenylphosphine oxide. The wipe off base coat layer, the gel nail polish layer, and the top coat layer are dried under an exposure of one of LED light, UV light, and sunlight that no wet sticky colloid is formed after the top coat layer is dried. The gel nail polish layer is adapted for being removed by directly wiping off the gel nail polish layer on the nail by using a rag, cotton, or tissue paper with the nail polish remover.

12 Claims, 3 Drawing Sheets

GEL NAIL POLISH AND ITS MANUFACTURING AND USING METHOD

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a gel nail polish, and more particularly to an easily wipeable gel nail polish and its manufacturing and using method, wherein the gel nail polish is dried out easily and can be directly wipe off by the polish remover without a complicate removing process.

Description of Related Arts

Gel nail polish are relative new in the market but has become really popular at nail salons and for nail painting enthusiasts in a short time. One of the popular gel nail polish is soft gel polish, which is often called as a soak off gel polish. The current soak off gel polish is long-lasting after applying on the nails, and always looks as new, wherein the soak off gel nails last on the nails for about 2 to 3 weeks without chipping, and they always look like they were just done. In addition, the soak off gel polish can be easily and directly painted on the natural nails in order to do the nail extension, and the user can easily change the color of the soak off gel nails by directly applying the traditional nail polish on the gel nails.

Accordingly, the users need to initially apply the soak off base coat nail polish on their nails as a first layer, and then apply at least one layers of soak off gel nail polish thereon as a second or third layer. Accordingly, the users need to apply a top coat nail polish on the third or fourth layer. In particular, in order to dry each layer on the nail, the nail must be exposed under a LED light or a UV light. In other words, each layer cannot be dried under the sunlight, so that it is inconvenience and money-wasting for the users to prepare and purchase the LED light or the UV light device. In addition, after each layer is dried, some wet sticky colloids will residue on the layer, so that the users must use alcohol to remove wet sticky colloids on each layer and to polish each layer after the following layer is applied. Therefore, the users need to spend at least 60 minutes to finish the four layers soak off gel polish structure, including soak off gel nail polish applying time, drying time, and residue removing time.

Furthermore, the removing process of the soak off gel nails is inconvenience and troublesome. Since the structure of the soak off gel polish layer is hard (having at least three-layered structure), the user cannot be directly wiped off by using a rag, cotton, or tissue paper with the nail polish remover, so the user needs to saturate a piece of cotton ball in the nail polish remover and place it on the nail until the cotton makes contact with the entire nail surface, and uses the aluminum foil to wrap around the fingertips until the cotton balls firmly attach on the nails. Wait for 5 to 7 minutes, a gap will naturally generate between the nails and the soak off gel polish layer, and then the user can use cuticle pusher or iron pusher to pop the soak off gel polish layer off the nail. Accordingly, after the soak off gel polish layer is removed from the nails, some residue gel is residued on the nails, so that the users must use the nail file or nail buffer to completely remove the residue gel from the nail. For such removing process, the users will spend at least 30 minutes to remove the soak off nail polish layer from their nails, and the nails will be damaged and thinned by frequently using the nail file or nail buffer.

SUMMARY OF THE PRESENT INVENTION

The invention is advantageous in that it provides a gel nail polish, wherein the gel nail polish is able to be directly wiped off from the nails by using a rag, cotton, or tissue paper with the nail polish remover without complicated removing process.

Another advantage of the invention is to provide a gel nail polish, wherein the removing process of the gel nail polish of the present invention is simple, so that no aluminum foils are needed to wrap around the fingertips, and also no additional auxiliary, such as a cuticle pusher or iron pusher is needed to pop the gel nail polish layer off the nail.

Another advantage of the invention is to provide a gel nail polish, wherein no wet sticky colloids will residue on the finished gel nail polish structure after the finished gel nail polish structure is dried, so that the users doesn't need to use alcohol to remove wet sticky colloids on the structure.

Another advantage of the invention is to provide a gel nail polish, wherein the gel nail polish can be easily and quickly dried after exposing under a light structure, and especially the light structure can be the natural sunlight.

Another advantage of the invention is to provide a gel nail polish, wherein a method of using the gel nail polish, including applying and removing method of the gel nail polish is time-saving and money saving for the user. In other words, the damages for the nails are reduced during the gel nail polish removing process.

Another advantage of the invention is to provide a gel nail polish, wherein no expensive and complicated structure is required to be employed in the present invention in order to achieve the above mentioned advantages. Therefore, the present invention successfully provides an economic and efficient solution to simply the applying and removing process for the gel nail polish.

Additional advantages and features of the invention will become apparent from the description which follows, and may be realized by means of the instrumentalities and combinations particular point out in the appended claims.

According to the present invention, the foregoing and other objects and advantages are attained by a gel nail polish composition which comprises a gel nail polish mixture and a color agent mixing with the gel nail polish mixture.

The gel nail polish mixture comprises first through fourth chemical elements, wherein the first through fourth chemical elements are aliphatic urethane acrylate, polymer acrylate oligomer, propoxylated neopentyl glycol diacrylate, and trimethylbenzoyl diphenylphosphine oxide.

In accordance with another aspect of the invention, the present invention comprises a method of manufacturing a gel nail polish, comprising the following steps:

(1) Provide first through fourth chemical elements.

(2) Dissolve the first chemical element and the second chemical element into the third chemical element to form a first mixture.

(3) Mix and stir the fourth chemical element into the first mixture to form a second mixture.

(4) Add and mix the color agent into the second mixture to form a final product of the gel nail polish.

(5) Fill the final product of the gel nail polish into a gel nail polish bottle and package the gel nail polish bottle with the gel nail polish therein, such that the gel nail polish is ready to use.

In accordance with another aspect of the invention, the present invention comprises a method of using a gel nail polish, comprising the following steps:

(A) Apply a wipe off base coat on the nail.

(B) Dry the wipe off base coat under an exposure of light to form a wipe off base coat layer.

(C) Apply a color coat of gel nail polish on the wipe off base coat layer.

(D) Dry the color coat of gel nail polish to form a gel nail polish layer.

(E) Apply a coat of gel nail polish top coat on the gel nail polish layer to form a top coat layer.

(F) Dry the top coat layer to form a finished gel nail polish structure, wherein when the top coat layer is dried, no wet sticky colloid is formed on the finished gel nail polish structure.

(G) When removing the finished gel nail polish structure, directly wipes off the finished gel nail polish structure by a rag, cotton, or tissue paper with the nail polish remover.

In accordance with another aspect of the invention, the present invention comprises a method of using a gel nail polish, comprising the following steps:

(a) Apply a color coat of gel nail polish on the nail.

(b) Dry the color coat of gel nail polish to form a gel nail polish layer.

(c) When removing the gel nail polish layer, directly wipes off the gel nail polish layer by a rag, cotton, or tissue paper with the nail polish remover.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

A gel nail polish of the present invention is adapted to being dried under an exposure of light. The user is able to remove the gel nail polish structure by directly wipe off the gel nail polish structure by a rag, cotton, or tissue paper with the nail polish remover without complicated removing process and auxiliary tools, which is a conventional nail polish removing process.

The gel nail polish according to the preferred embodiment of the present invention is illustrated, wherein the gel nail polish composition comprises a gel nail polish mixture and a color agent mixing with the nail polish mixture. The gel nail polish mixture comprises first through fourth chemical elements, wherein the first through fourth chemical elements are aliphatic urethane acrylate, polymer acrylate oligomer, propoxylated neopentyl glycol diacrylate, and trimethylbenzoyl diphenylphosphine oxide respectively. Accordingly, an amount of the first chemical element (aliphatic urethane acrylate) has a range of 57.6-69.9% by weight. An amount of the second chemical element (polymer acrylate oligomer) has a range of 16.4-19.8% by weight. An amount of the third chemical element (propoxylated neopentyl glycol diacrylate) has a range of 12.7-15.4% by weight. An amount of the fourth chemical element (trimethylbenzoyl diphenylphosphine oxide) has a range of 4.1-4.9% by weight. In particular, a weight ratio of the first through fourth chemical element is 63.5:18:14:4.5.

Accordingly, the gel nail polish mixture is a dryable mixture being dried under an exposure of LED light, UV light, or sunlight.

Figure 1:
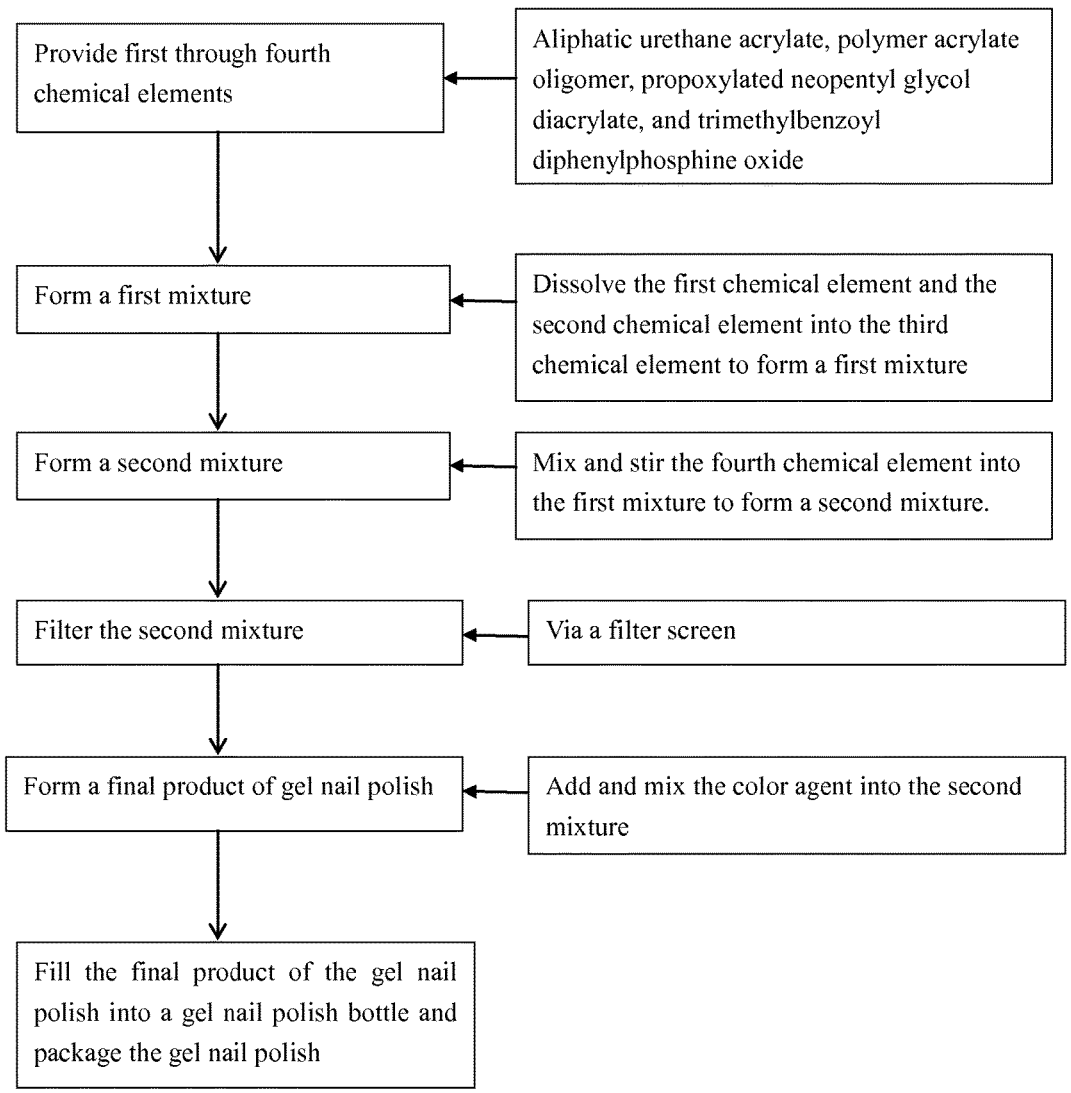
FIG. 1 is a block diagram of a method of manufacturing a gel nail polish according to a preferred embodiment of the present invention.

Referring to FIG. 1 of the drawings, the present invention provides a method of manufacturing the gel nail polish, wherein the manufacturing method comprises the following steps:

(1) Provide first through fourth chemical elements. Accordingly, the first through fourth chemical element and their weight ratio are shown above. (2) Dissolve the first chemical element and the second chemical element into the third chemical element to form a first mixture. Accordingly, the first chemical element and the second chemical element are preferably stirred into the third chemical element for 40 minutes under 60° C. in order to ensure the first chemical element and the second chemical element to be well-mixed into the third chemical element. In other words, the first and second chemical element are gradually heated up from room temperature to 60° C. when the first and second chemical element are added and dissolve into the third chemical element.

(3) Mix and stir the fourth chemical element into the first mixture to form a second mixture. In addition, the second mixture is preferably stirred for 30 minutes under room temperature to ensure the fourth chemical element are well-mixed into the first mixture. It is worth mentioning that after the fourth chemical element is dissolved in the first mixture, the second mixture should be cooled down from 60° C. back to the room temperature.

(4) Add and mix the color agent into the second mixture to form a final product of the gel nail polish. Accordingly, the color agent contains color pigments to form the final product of the gel nail polish with a desired color.

(5) Fill the final product of the gel nail polish into a gel nail polish bottle and package the gel nail polish bottle with the gel nail polish therein, such that the gel nail polish is ready to use.

According to the preferred embodiment, before the step (4), the manufacturing method further comprises a step of filtering the second mixture to remove residues in the second mixture before the color agent is added thereinto. Accordingly, the second mixture is filtered by screen, such as a 200 mesh gauze screen, to ensure the standardized particle size of the third mixture.

Figure 2:
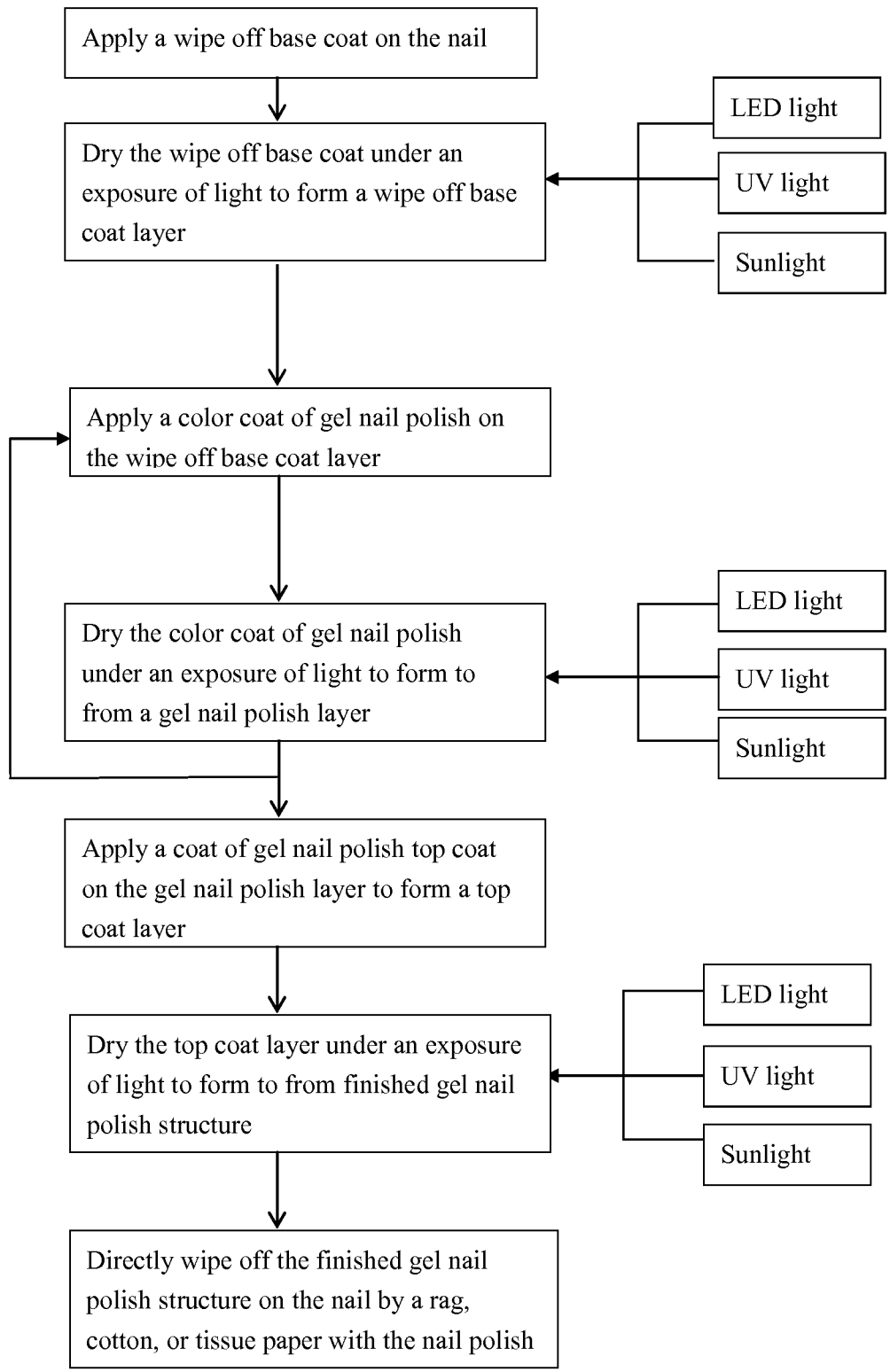
FIG. 2 is a block diagram of a method of using a gel nail polish according to the above preferred embodiment of the present invention.

Referring to FIG. 2 of the drawings, the present invention further provides a method of using the gel nail polish, wherein the using method comprises the following steps:

(A) Apply a wipe off base coat on the nail.

(B) Dry the wipe off base coat under an exposure of light to from a wipe off base coat layer.

(C) Apply a color coat of gel nail polish on the wipe off base coat layer.

(D) Dry the color coat of gel nail polish to form a gel nail polish layer.

(E) Apply a coat of gel nail polish top coat on the gel nail polish layer to from a top coat layer.

(F) Dry the gel nail polish top coat to from a finished gel nail polish structure, wherein when the gel nail polish top coat is dried, no wet sticky colloid is formed on the finished gel nail polish structure.

The wipe off base coat layer, the gel nail polish layer, and the top coat layer and are completely dried under an exposure of LED light for 30 to 60 seconds, under an exposure of UV light for 2 minutes, or under an exposure of sunlight for 1 to 2 minutes. It is worth mentioning that there is no wet sticky colloid formed on the finished gel nail polish structure, such that the user does not need to use alcohol to remove wet sticky colloids on the finished gel nail polish structure formed by the conventional soak off gel nail polish.

If necessary, repeat the steps (D) and (E) to apply a second color coat of gel nail polish on the nail. The second coat is applied on the first gel nail polish layer after the first gel nail polish layer is dried. The second coat is dried under an exposure of light to integrally form the second layer on the first gel nail polish layer as one single layer structure. It is worth mentioning that the finished gel nail polish structure are three-layered or four-layered gel nail polish, which is determined by the number of color gel nail polish layer applied on the nails.

(G) When removing the gel nail polish layer, directly wipes off the finished gel nail polish structure by a rag, cotton, or tissue paper with the nail polish remover. It is worth mentioning that the finished gel nail polish structure can be kept on the nail for 7 to 14 days as it is originally applied thereon.

According to the preferred embodiment, the gel nail polish is able to directly wipe off from the nail without using the aluminum foil to wrap around the fingertips with the cotton balls saturated with the nail polish remover, so the user can prevent spending lots of time to wait until a gap generated between the nails and the finished gel nail polish structure. And, the user doesn't need to use cuticle pusher or iron pusher to pop the gel nail polish layer off the nail, so as to prevent the nails being uneven and not smooth. In addition, the user also doesn't need to nail file or nail buffer to completely remove the residue gel from the nail, so as to prevent the nails being thinner. In other words, the removing process of the gel nail polish of the present invention can dramatically reduce the damage happened on the nails.

It is worth mentioning that the conventional gel nail polish cannot be dried by exposing under the natural sunlight. And, after the top coat layer is dried, some wet sticky colloids will residue on the layer, so that the users must use alcohol to remove wet sticky colloids on the gel nail polish layer. Therefore, the gel nail polish of the present invention allows the user to save more time and money to remove and apply the gel nail polish on their nails.

Figure 3:
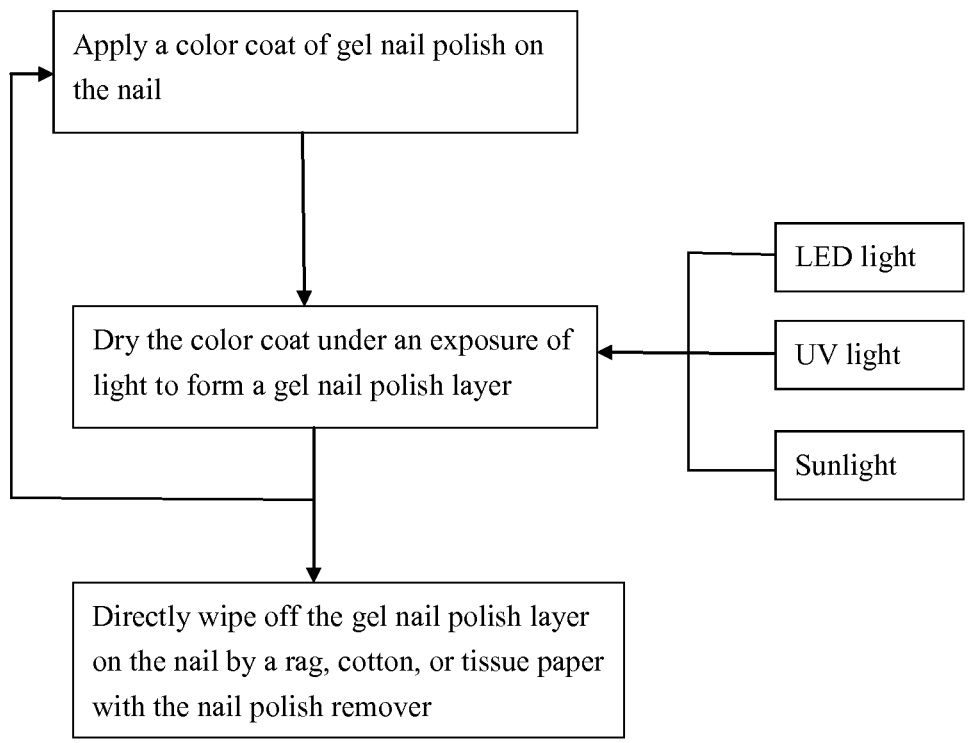
FIG. 3 is a block diagram of an alternative mode of using a gel nail polish according to the above preferred embodiment of the present invention.

Referring to FIG. 3 of the drawings, the present invention further provides an alternative mode of a method of using the gel nail polish, wherein the using method comprises the following steps:

(A) Apply a color coat of gel nail polish on the nail. The user is able to apply a color coat of gel nail polish from the gel nail polish bottle via a conventional method. It is worth mentioning that no base coat and top coat is required before and after the gel nail polish layer is formed on the nail. (B) Dry the color coat of the gel nail polish under an exposure of light to form the gel nail polish layer, wherein when the gel nail polish layer is dried, no wet sticky colloid is formed on the gel nail polish layer. The gel nail polish layer is completely dried under an exposure of LED light for 30 to 60 seconds, under an exposure of UV light for 2 minutes, or under an exposure of sunlight for 1 to 2 minutes. It is worth mentioning that there is no wet sticky colloid formed on the gel nail polish layer, such that the user does not need to use alcohol to remove wet sticky colloids on the gel nail polish layer formed by the conventional nail polish. If necessary, repeat the steps (A) and (B) to apply a second color coat of gel nail polish on the nail. The second color coat is applied on the first gel nail polish layer after the first gel nail polish layer is dried. The second coat is also dried under an exposure of light to integrally form the second layer on the first gel nail polish layer as one single layer structure. The double layered gel nail polish is opaque and makes the color more intense and even on the nail.

(C) When removing the gel nail polish layer, directly wipes off the gel nail polish layer by a rag, cotton, or tissue paper with the nail polish remover. It is worth mentioning that the gel nail polish layer can be kept on the nail for 7 to 14 days as it is originally applied thereon.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for using a gel nail polish, consisting essentially of:

(a) providing a gel nail polish which consists essentially of 57.6-69.9% by weight of an aliphatic urethane acrylate, 16.4-19.8% by weight of a polymer acrylate oligomer, 12.7-15.4% by weight of a propoxylated neopentyl glycol diacrylate, and 4.1-4.9% by weight of a trimethylbenzoyl diphenylphosphine oxide;

(b) applying a coat of said gel nail polish on a nail;

(c) drying said gel nail polish layer on said coat of gel nail polish under an exposure of natural sunlight for 1 to 2 minutes to form a gel nail polish layer with no wet sticky colloid on said nail, wherein no base coat and top coat is required before and after said gel nail polish layer is formed on said nail and said gel nail polish layer is able to be kept on said nail for 7 to 14 days; and (d) directly wiping off said gel nail polish layer from said nail by a rag, a cotton, or a tissue paper with a nail polish remover so as to directly remove said gel nail polish layer from said nail without the needs of using metal foil to wrap around said nail, using cuticle pusher to pop said gel nail polish layer off said nail, and using nail file to remove residue gel from said nail.

2. The method, as recited in claim 1, wherein a weight ratio of said aliphatic urethane acrylate, said polymer acrylate oligomer, said propoxylated neopentyl glycol diacrylate, and said trimethylbenzoyl diphenylphosphine oxide is 63.5:18:14:4.5.

3. The method, as recited in claim 1, wherein said gel nail polish is manufactured by the following steps:
  dissolving said aliphatic urethane acrylate and said polymer acrylate oligomer in said propoxylated neopentyl glycol diacrylate by stirring and gradually heating up said aliphatic urethane acrylate and said polymer acrylate oligomer into said propoxylated neopentyl glycol diacrylate from room temperature to 60° C. for 40 minutes to form a first mixture;
  (ii) dissolving said trimethylbenzoyl diphenylphosphine oxide in said first mixture by mixing and stirring said trimethylbenzoyl diphenylphosphine oxide into said first mixture for 30 minutes to form a second mixture, and cooling down said second mixture from 60° C. back to the room temperature;
  (iii) filtering said second mixture to remove residues in said second mixture; and
  (iv) adding and mixing a color agent into said second mixture for form said gel nail polish.

4. The method, as recited in claim 2, wherein said gel nail polish is manufactured by the following steps:
  (i) dissolving said aliphatic urethane acrylate and said polymer acrylate oligomer in said propoxylated neopentyl glycol diacrylate by stirring and gradually heating up said aliphatic urethane acrylate and said polymer acrylate oligomer into said propoxylated neopentyl glycol diacrylate from room temperature to 60° C. for 40 minutes to form a first mixture;
  (ii) dissolving said trimethylbenzoyl diphenylphosphine oxide in said first mixture by mixing and stirring said trimethylbenzoyl diphenylphosphine oxide into said first mixture for 30 minutes to form a second mixture, and cooling down said second mixture from 60° C. back to the room temperature;
  (iii) filtering said second mixture to remove residues in said second mixture; and
  (iv) adding and mixing a color agent into said second mixture for form said gel nail polish.

5. A method for using a gel nail polish, consisting essentially the steps of:
  (a) providing a gel nail polish which consists essentially of 57.6-69.9% by weight of an aliphatic urethane acrylate, 16.4-19.8% by weight of a polymer acrylate oligomer, 12.7-15.4% by weight of a propoxylated neopentyl glycol diacrylate, and 4.1-4.9% by weight of a trimethylbenzoyl diphenylphosphine oxide;
  (b) applying a coat of said gel nail polish on a nail;
  (c) drying said gel nail polish layer on said coat of gel nail polish under an exposure of LED light for 30 seconds to less than 60 seconds to form a gel nail polish layer with no wet sticky colloid on said nail, wherein no base coat and top coat is required before and after said gel nail polish layer is formed on said nail and said gel nail polish layer is able to be kept on said nail for 7 to 14 days; and
  (d) directly wiping off said gel nail polish layer from said nail by a rag, a cotton or a tissue paper with a nail polish remover so as to directly remove said gel nail polish layer from said nail without the needs of using metal foil to wrap around said nail, using cuticle pusher to pop said gel nail polish layer off said nail, and using nail file to remove residue gel from said nail.

6. The method, as recited in claim 5, wherein a weight ratio of said aliphatic urethane acrylate, said polymer acrylate oligomer, said propoxylated neopentyl glycol diacrylate, and said trimethylbenzoyl diphenylphosphine oxide is 63.5:18:14:4.5.

7. The method, as recited in claim 5, wherein said gel nail polish is manufactured by the following steps:
  (i) dissolving said aliphatic urethane acrylate and said polymer acrylate oligomer in said propoxylated neopentyl glycol diacrylate by stirring and gradually heating up said aliphatic urethane acrylate and said polymer acrylate oligomer into said propoxylated neopentyl glycol diacrylate from room temperature to 60° C. for 40 minutes to form a first mixture;
  (ii) dissolving said trimethylbenzoyl diphenylphosphine oxide in said first mixture by mixing and stirring said trimethylbenzoyl diphenylphosphine oxide into said first mixture for 30 minutes to form a second mixture, and cooling down said second mixture from 60° C. back to the room temperature;
  (iii) filtering said second mixture to remove residues in said second mixture; and
  (iv) adding and mixing a color agent into said second mixture for form said gel nail polish.

8. The method, as recited in claim 6, wherein said gel nail polish is manufactured by the following steps:
  (i) dissolving said aliphatic urethane acrylate and said polymer acrylate oligomer in said propoxylated neopentyl glycol diacrylate by stirring and gradually heating up said aliphatic urethane acrylate and said polymer acrylate oligomer into said propoxylated neopentyl glycol diacrylate from room temperature to 60° C. for 40 minutes to form a first mixture;
  (ii) dissolving said trimethylbenzoyl diphenylphosphine oxide in said first mixture by mixing and stirring said trimethylbenzoyl diphenylphosphine oxide into said first mixture for 30 minutes to form a second mixture, and cooling down said second mixture from 60° C. back to the room temperature;
  (iii) filtering said second mixture to remove residues in said second mixture; and
  (iv) adding and mixing a color agent into said second mixture for form said gel nail polish.

9. A method for using a gel nail polish, consisting essentially the steps of:
  (i) providing a gel nail polish which consists essentially of 57.6-69.9% by weight of an aliphatic urethane acrylate, 16.4-19.8% by weight of a polymer acrylate oligomer, 12.7-15.4% by weight of a propoxylated neopentyl glycol diacrylate, and 4.1-4.9% by weight of a trimethylbenzoyl diphenylphosphine oxide;
  (ii) applying a coat of said gel nail polish on a nail;
  (iii) drying said gel nail polish layer on said coat of gel nail polish under an exposure of UV light for 2 minutes to form a gel nail polish layer with no wet sticky colloid on said nail, wherein no base coat and top coat is required before and after said gel nail polish layer is formed on said nail and said gel nail polish layer is able to be kept on said nail for 7 to 14 days; and
  (iv) directly wiping off said gel nail polish layer from said nail by a rag, a cotton or a tissue paper with a nail polish remover so as to directly remove said gel nail polish layer from said nail without the needs of using metal foil to wrap around said nail, using cuticle pusher to pop said gel nail polish layer off said nail, and using nail file to remove residue gel from said nail.

10. The method, as recited in claim 9, wherein a weight ratio of said aliphatic urethane acrylate, said polymer acrylate oligomer, said propoxylated neopentyl glycol diacrylate, and said trimethylbenzoyl diphenylphosphine oxide is 63.5:18:14:4.5.

11. The method, as recited in claim 9, wherein said gel nail polish is manufactured by the following steps:
   (i) dissolving said aliphatic urethane acrylate and said polymer acrylate oligomer in said propoxylated neopentyl glycol diacrylate by stirring and gradually heating up said aliphatic urethane acrylate and said polymer acrylate oligomer into said
   (ii) propoxylated neopentyl glycol diacrylate from room temperature to 60° C. for 40 minutes to form a first mixture;
   (iii) dissolving said trimethylbenzoyl diphenylphosphine oxide in said first mixture by mixing and stirring said trimethylbenzoyl diphenylphosphine oxide into said first mixture for 30 minutes to form a second mixture, and cooling down said second mixture from 60° C. back to the room temperature;
   (iv) filtering said second mixture to remove residues in said second mixture; and
   (v) adding and mixing a color agent into said second mixture for form said gel nail polish.

12. The method, as recited in claim 10, wherein said gel nail polish is manufactured by the following steps:
   (i) dissolving said aliphatic urethane acrylate and said polymer acrylate oligomer in said propoxylated neopentyl glycol diacrylate by stirring and gradually heating up said aliphatic urethane acrylate and said polymer acrylate oligomer into said propoxylated neopentyl glycol diacrylate from room temperature to 60° C. for 40 minutes to form a first mixture;
   (ii) dissolving said trimethylbenzoyl diphenylphosphine oxide in said first mixture by mixing and stirring said trimethylbenzoyl diphenylphosphine oxide into said first mixture for 30 minutes to form a second mixture, and cooling down said second mixture from 60° C. back to the room temperature;
   (iii) filtering said second mixture to remove residues in said second mixture; and
   (iv) adding and mixing a color agent into said second mixture for form said gel nail polish.

* * * * *